United States Patent [19]

Krämer et al.

[11] Patent Number: 5,059,306
[45] Date of Patent: Oct. 22, 1991

[54] PROCESS FOR REMOVING PURE AROMATICS

[75] Inventors: Hans-Joachim Krämer, Dormagen; Bruno Schulwitz, Cologne; Werner Horlitz, Dormagen; Peter M. Lange, Leverkusen; Alfred Mitschker, Odenthal-Holz, all of Fed. Rep. of Germany

[73] Assignee: Bayer Aktiengesellschaft, Leverkusen, Fed. Rep. of Germany

[21] Appl. No.: 541,555

[22] Filed: Jun. 21, 1990

Related U.S. Application Data

[63] Continuation of Ser. No. 221,808, Jul. 20, 1988.

[30] Foreign Application Priority Data

Jul. 30, 1987 [DE] Fed. Rep. of Germany ....... 3725228

[51] Int. Cl.$^5$ ................................................ C10G 7/08
[52] U.S. Cl. .................................. 208/313; 208/311; 585/830; 585/833
[58] Field of Search ................. 208/311, 313; 585/833, 585/830

[56] References Cited

U.S. PATENT DOCUMENTS

| | | | |
|---|---|---|---|
| 2,780,358 | 2/1957 | Mosesman et al. | 585/830 |
| 3,207,692 | 9/1965 | Van Kleet et al. | 208/313 |
| 3,216,928 | 11/1965 | Paulson | 585/830 |
| 3,338,823 | 8/1967 | Voetter | 208/325 |
| 3,409,691 | 11/1968 | Small | 585/830 |

OTHER PUBLICATIONS

"Distillation", Van Winkle, McGraw-Hill, 1967, pp. 604-619.

Primary Examiner—Curtis R. Davis
Assistant Examiner—William Diemler
Attorney, Agent, or Firm—Sprung Horn Kramer & Woods

[57] ABSTRACT

In the removal of pure aromatics from aromatic-containing hydrocarbon mixtures by liquid-phase extraction or extractive distillation using a selective solvent, the specific cost of separation can be reduced at the same yield of aromatics or the yield of aromatics can be increased at the same specific cost of separation if the liquid-phase extraction or the extractive distillation is carried out in the presence of a reactive solid. At the same time, substantially aromatic-free raffinates are obtained.

6 Claims, 1 Drawing Sheet

PROCESS FOR REMOVING PURE AROMATICS

This is a continuation of application Ser. No. 221,808, filed July 20, 1988, now pending.

BACKGROUND OF THE INVENTION

The invention relates to a process for removing pure aromatic hydrocarbons from hydrocarbon mixtures containing these compounds by extraction in the presence of reactive substances, substantially aromatic-free raffinates being obtained at the same time.

The starting materials for the removal according to the invention, of pure aromatics are mixtures of aromatic and nonaromatic hydrocarbons from which the pure aromatics cannot be removed by simple thermal distillation as a consequence of similar boiling points. The mixtures may contain the aromatics, for example benzene, toluene and xylene, either together or individually. Mixtures of the type mentioned are produced, for example, in refineries and petrochemical plants.

It is known that nonaromatics can be separated from aromatics by extraction using selective solvents. Extraction is taken to mean both classical liquid-phase extraction and extractive distillation. In both methods, the aromatics are selectively extracted from the hydrocarbon by a solvent. In liquid-phase extraction, the removal of the low-aromatic raffinate from the high-aromatic solvent takes place by mechanical separation in an extractor; in extraction distillation, the separation takes place by distillation in a column. In both cases, isolation of the pure aromatic(s) takes place in a downstream column (stripper) by distillation of the aromatic(s) from the solvent. The low-aromatic solvent is fed back from the stripper bottom into the liquid-phase extractor or into the extractive-distillation column.

In both process variants for obtaining pure aromatics from aromatic-containing hydrocarbon mixtures, the specific cost of separation is determined by the following factors:

a) by the aromatic concentration in the starting mixture, b) by the aromatic yield, and c) by the quality demands on the pure aromatic(s) or on the raffinate.

For example, in the case where the aromatic concentration of the input stream is constant and the quality demands on the pure aromatic(s) with respect to nonaromatics and traces of solvent, and the quality demands on the raffinate with respect to traces of solvent and aromatic content likewise remain the same, the energy cost increases with the desired yield of aromatics. The ideal point from the process engineering point of view is then determined by the energy costs on the one hand and by the proceeds from sale or further processing of the aromatics and the raffinate on the other hand.

The present invention now makes it possible to reduce the specific cost of separation at the same aromatic yield or to increase the aromatic yield at the same specific cost of separation, it also being possible, if desirable, to produce operating states between the extreme values mentioned. Since legal restrictions with respect to the aromatic content in carburettor fuel are expected in the future, it is necessary to reduce the aromatic content in the low-aromatic raffinate as far as possible, which at the same time means preferably giving priority to increased aromatic yield at the same specific cost of separation.

SUMMARY OF THE INVENTION

A process for removing aromatics from hydrocarbon mixtures by extraction either liquid-phase extraction or extractive distillation using a selective solvent has now been found which is characterized in that the extraction is carried out in the presence of a reactive solid.

BRIEF DESCRIPTION OF THE DRAWING

The accompanying drawing shows a preferred variant of carrying out the invention with the aid of an extractive-distillation column (1), a stripper column (6) and a rectifying column (14).

DETAILED DESCRIPTION OF THE INVENTION

Figure 1:
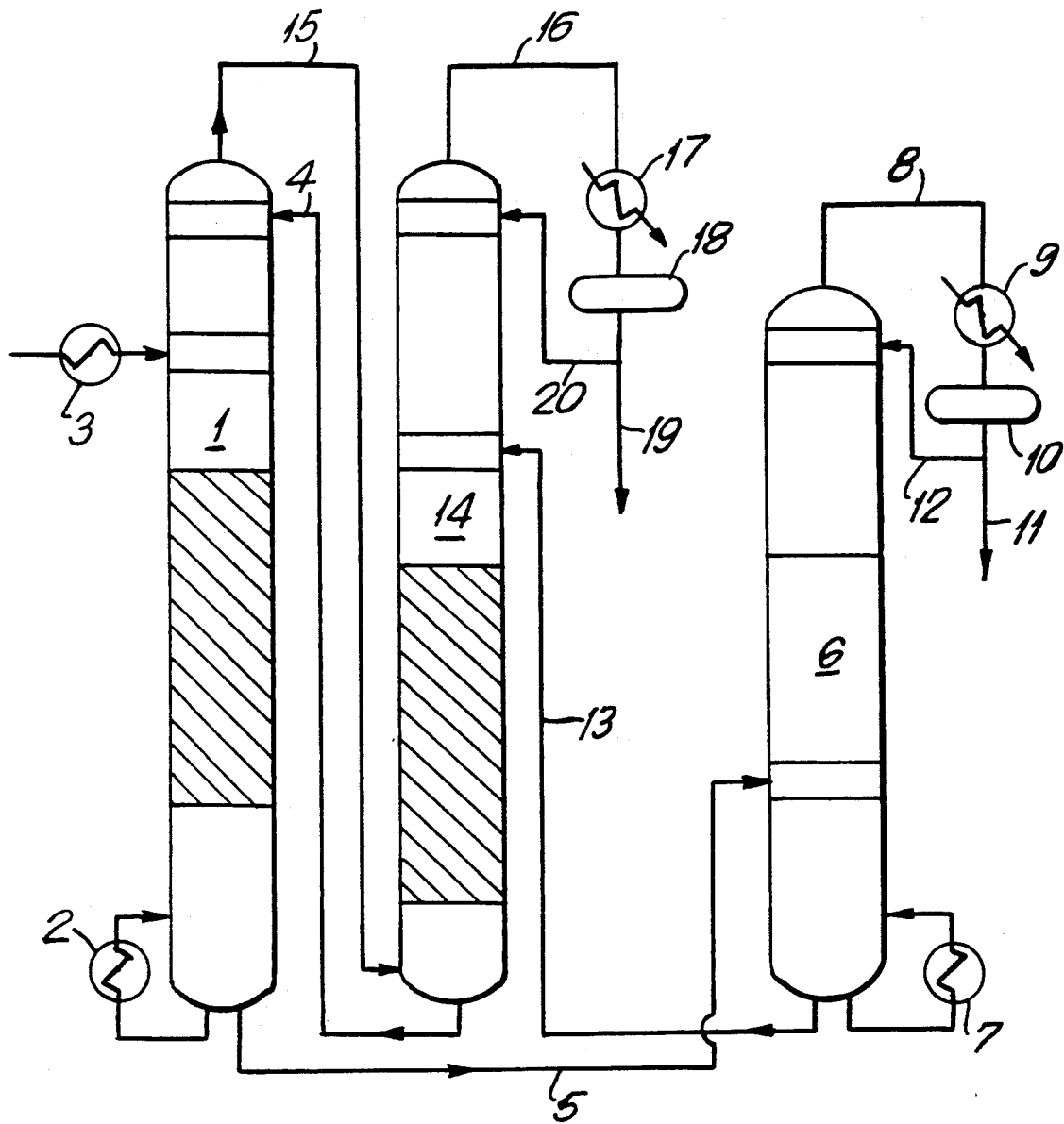

Reactive solids for the process according to the invention are taken to mean those which only undergo interaction with certain components of a mixture to be seperated, whereas they only undergo weak interactions, or none at all, with the remaining components of the mixture. Interactions which may be mentioned in this connection are, for example, the swelling behavior of a solid with certain components in the mixture and the elution behavior of the solid swollen with certain suitable components. Electronic interactions can also contribute to improved extraction in the presence of the reactive solids. If, for example, reactive solids are introduced into an extraction column at a suitable point, improved resolution is possible if the extractant used is capable of eluting certain enriched components of these reactive solids. The reactive solid is also capable of undergoing interactions with the solvent and additionally forming a stationary phase.

The reactive solids to be employed according to the invention can easily be prepared, for example by classical bead polymerization, as described in Houben-Weyl Vol. 14/1 pp. 133 ff. Thus, the solids to be employed according to the invention are obtained if, for example, styrene is reacted with varying amounts of a porogen in the presence of 2-85% by weight of divinylbenzene (DVB), if appropriate in the form of technical grade DVB and varying amounts of a porogen or technical grade DVB alone. The suitable porogens are known to those skilled in the art. So-called precipitants or swelling agents, or mixtures thereof, can be employed to produce macroporous reactive solids.

The use of other monomers is also conceivable if the interactions, such as, for example, the swelling behavior, of the polymers thus obtainable without aromatics are thereby retained. However, base resins for ion exchangers based on styrene/DVB are preferred, not least because they are available industrially in appropriate amounts. The reactive solids can be used in gel form or in macroporous form. Usually, however, the use of macroporous base solids produces better separation results. The degree of crosslinking of the parent substances can be between 2 and 85%. As is known, the surface area of macroporous base solids increases with greater crosslinking, so that more intimate contact between the aromatics and the reactive solid is therefore possible. For this reason, base solids which contain 40-85% by weight of technical grade DVB are particularly preferred.

The extraction in the preferred form of an extractive distillation is described below as an example: in a stream of vapor, comprising aliphatic hydrocarbons and aromatics, the aromatic components undergo strong interactions with reactive solids based on a styrene-divinylbenzene polymer, whereas the aliphatic hydrocarbons undergo virtually no interactions with the reactive solids mentioned. The selective solvent, which is, in addition, employed here in countercurrent, elutes, in addition to the extractive distillation effect which is already known, proportions of the aromatics from the reactive substances. The separation efficiency is thus significantly increased at the same energy cost.

In the case of classical liquid-phase extraction, reactive solids of this type are introduced into the contact chambers of an extractor.

It has proven advantageous to immobilize the reactive solids, for example within tetrahedral wire gauzes, and to introduce these wire gauzes as packing elements into extractive-distillation columns or contact chambers of extractors. The tetrahedral wire gauzes are advantageously only partly filled with the reactive solid in order to permit swelling.

In a further example, wire gauzes can again be filled with the reactive solids and subsequently rolled up so that suitable packing elements are again thereby produced. In place of wire gauzes, reactive solids of this type can alternatively be rolled into porous plastic mats which can then serve as packing elements. It is furthermore conceivable to fill commercially available packing elements, such as Rasching rings or Berl saddles, with reactive solids so that these reactive solids are immobilized on the packing elements, whereafter filled packing elements of this type are employed in the manner described.

Selective solvents which can be employed are, for example: N-methyl-pyrrolidone, N-formyl-morpholine, sulpholane and acetonitrile.

The other process parameters to be set during the extraction (classical liquid-phase extraction or extractive distillation), such as temperature, pressure, flow rate, inter alia, are known to those skilled in the art.

It is likewise known to those skilled in the art to connect a stripper to the actual extraction apparatus (extractor or extractive-distillation column). In the case of extractive distillation, this may be described with reference to an example and the appended figure:

A benzene fraction is fed via line (3) to the upper part of an extractive-distillation column (1) equipped with circulation heating (2) for the column bottom. The extractive solvent is fed to (1) via line (4) above (3). A bottom stream is fed via line (5) to the stripper column (6) equipped with circulation heating (7) for the column bottom and separated therein into pure benzene and regenerated extractive solvent. The pure benzene is withdrawn as a head stream via line (8), condenser (9), collecting vessel (10) and line (11). Line (12) serves to adjust the return ratio. The regenerated extractive solvent is fed via line (13) to a rectifying column (14) for the extractive distillation. (13) is charged at the lower end with the head stream from (1) via line (15). The aromatic-free raffinate is withdrawn from (14) as a head stream via line (16), condenser (17), collecting vessel (18) and line (19). Line (20) serves to adjust the return ratio. (14) and, where appropriate, also (1) are provided according to the invention with reactive solids.

EXAMPLE

In a continuous laboratory experiment, 580 g/l of a benzene fraction (about 80% by weight of benzene and about 20% by weight of nonaromatics) were separated into pure benzene and a low-benzene raffinate (B raffinate) in an extractive-distillation column and a downstream stripper column with the aid of the solvent N-methyl-pyrrolidone (NMP). The extractive-distillation column had a theoretical tray number of 48. The product route was as shown in the figure.

The extractive-distillation column was packed with tetrahedral gauze packing elements, the gauze packing elements containing macroporous styrene-divinylbenzene bead polymer. The gauze packing elements were introduced into the region of the extraction zone, i.e. below the NMP addition point, as shown by the figure.

In a comparison experiment, gauze packing elements were likewise introduced, but these contained slightly acidic, porous ion exchangers based on Lewatite CNP 80.

The following results were obtained:

|  | Experiment according to the invention | Comparison experiment |
| --- | --- | --- |
| NMP: benzene fraction ratio | 3:1 | 3:1 |
| Nonaromatics in the benzene | 210 ppm | 150 ppm |
| Benzene in the B raffinate | 0.7% by wt. | 5.1% by wt. |
| Benzene yield | 99.8% | 99.8% |

What is claimed is:

1. In a process for removing aromatics from hydrocarbon mixtures by extraction with a selective solvent, said extraction being a liquid-phase extraction or extractive distillation, the improvement wherein the liquid-phase extraction or extractive distillation is carried out in the presence of solid base resins for ion exchangers said resins being styrene-divinylbenzene bead polymers containing 2-85% by weight of divinylbenzene.

2. A process according to claim 1, wherein the solid base resin is introduced as rolled porous plastic mats into an extractive-distillation column or into the contact chambers of an extractor.

3. A process according to claim 1, wherein the extraction is carried out in the presence of packing elements which are closed wire gauzes into which the solid base resin has been introduced.

4. A process according to claim 1, characterized in that the styrene-divinylbenzene bead polymers are used in macroporous form.

5. A process according to claim 1, characterized in that the styrene-divinylbenzene polymers used contain 40-85% by weight of divinylbenzene.

6. The process according to claim 1, said extraction being a liquid-phase extraction.

* * * * *